United States Patent [19]

Leapheart

[11] Patent Number: 5,214,169
[45] Date of Patent: May 25, 1993

[54] N-(2,3-EPOXYCYCLOPENTYL) CARBAMATE DERIVATIVES

[75] Inventor: Theophilus F. Leapheart, Midland, Mich.

[73] Assignee: Merrell Dow Pharmaceuticals Inc., Cincinnati, Ohio

[21] Appl. No.: 877,352

[22] Filed: Apr. 30, 1992

Related U.S. Application Data

[60] Continuation of Ser. No. 752,886, Aug. 26, 1991, abandoned, which is a continuation of Ser. No. 609,125, Nov. 1, 1990, abandoned, which is a continuation of Ser. No. 436,969, Nov. 15, 1989, abandoned, which is a division of Ser. No. 185,635, Apr. 25, 1988, abandoned.

[51] Int. Cl.$^5$ .......................... C07D 303/40
[52] U.S. Cl. .................. 549/546; 548/221; 560/115; 564/413
[58] Field of Search .......................... 549/546

[56] References Cited

U.S. PATENT DOCUMENTS

| | | | |
|---|---|---|---|
| 2,933,383 | 4/1960 | Lambrech | 71/106 |
| 3,874,939 | 4/1975 | Fraley | 71/106 |
| 4,003,735 | 1/1977 | Czajkowski | 71/106 |
| 4,021,224 | 5/1977 | Pallos | 71/106 |
| 4,661,217 | 4/1987 | Degner | 560/115 |
| 4,868,315 | 9/1989 | LeTourneau et al. | 546/273 |

FOREIGN PATENT DOCUMENTS 0127143  5/1984  European Pat. Off.

OTHER PUBLICATIONS

J. of Med. Chem., 1974, vol. 17, No. 6, pp. 578+ Vince, R. and Daluge, S. "Puromycin Analogs . . . ".
Hilpert, H. et al., Helv. Chim. Acta 1987, vol 70(2) (dated Jan. 19, 1987) pp. 390-395 and CA 107:217516k.
Chemische Berichte, vol. 98, pp. 1097-1110 (1965) Müeller et al.

*Primary Examiner*—Mukund J. Shah
*Assistant Examiner*—Philip Daltow
*Attorney, Agent, or Firm*—J. Michael Dixon

[57] ABSTRACT

The present invention as directed to a new class of N-(2,3-epoxycyclopentyl) carbamate derivatives as described by Formula V below, that are useful as chemical intermediates in the production of a new class of antihypertensives:

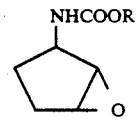

Formula V

4 Claims, No Drawings

N-(2,3-EPOXYCYCLOPENTYL) CARBAMATE DERIVATIVES

CROSS-REFERENCE TO RELATED APPLICATION

This is a continuation of application Ser. No. 07/752,886, filed Aug. 26, 1991, now abandoned, which is a continuation of application Ser. No. 07/609,125, filed Nov. 1, 1990, now abandoned, which is a continuation of Ser. No. 07/436,969, filed Nov. 15, 1989, now abandoned, which is a divisional of Ser. No. 07/185,635, filed Apr. 25, 1988, now abandoned.

The present invention pertains to carbamate derivatives having utility as intermediates in the production of pharmaceutical compounds. A further aspect of the present invention is directed to their use in the manufacture of pharmaceutical compounds.

European Patent Application 0 127 143 discloses a class of aryloxy cycloalkanolaminoalkyl aryl ketones which have utility as antihypertensive agents. One class of these compounds is produced utilizing a 2-amino-5-phenoxycyclopentanol intermediate of the formula:

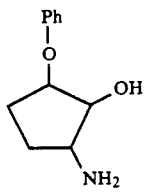

Formula I wherein Ph represents a phenyl ring which can be substituted with up to 3 substituents selected from the group consisting of a ($C_1$-$C_6$) alkyl, a $C_1$-$C_6$ alkoxy, halogen, nitro, trifluoromethyl, and trifluomethoxy. The present invention is directed to a method for producing this intermediate.

As used in this application:

a) The term $C_{1-6}$ alkyl refers to a straight chain, branched, or cyclic alkyl group containing up to 6 carbon atoms. Likewise the term $C_{1-12}$ alkyl refers to a straight chain, cyclic or branched alkyl group containing up to 12 carbon atoms. Representative examples of suitable alkyl groups include, methyl, ethyl, propyl, isopropyl, n-butyl, t-butyl, pentyl, hexyl, heptyl, octyl, cyclopropyl, and cyclopentyl.

b) The term halogen refers to a fluorine, bromine, chlorine or iodine atom.

c) The term $C_{1-6}$ alkoxy refers to a straight chain or branched alkoxy group containing up to 6 carbon atoms. Likewise the term $C_{1-12}$ alkoxy refers to a straight chain or branched alkoxy group containing up to 12 carbon atoms. Representative examples of suitable alkoxy groups include methoxy, ethoxy, propoxy, isopropoxy, butoxy, pentoxy, hexyloxy, heptyloxy, and octyloxy.

d) The term hydroxy in this application refers to the following substituent —OH.

e) The term nitro refers to the following substituent —NO$_2$.

f) The term trifluoromethyl refers to the following substituent —CF$_3$.

g) The term trifluoromethoxy refers to the following substituent —OCF$_3$.

h) The term aryl or substituted aryl refers to benzene or a benzene substituted at up to 3 positions with substituents such as $C_{1-6}$ alkyl, $C_{1-6}$ alkoxy, nitro, trifluoromethyl, hydroxy, or trifluromethoxy.

The starting materials in the synthesis of the present invention are known in the art. They are a 1,3-cylopentadiene which can be described by the following formula:

Formula II and a substituted carbamate of the formula:

NH$_2$COOR    Formula III wherein R is represented by a $C_1$-$C_{12}$ alkyl, aryl or a substituted aryl substituent. The substituent representing R is not retained in the final product. Thus, it is immaterial which particular alkyl or aryl carbamate that is utilized. However, $C_{1-6}$ alkyls are currently utilized.

They are reacted together in order to produce a N-cyclopentenyl carbamate of the formula:

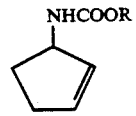

Formula IV wherein R is represented by a ($C_1$-$C_{12}$) alkyl, aryl, or substituted aryl substituent.

The reaction between the cyclopentadiene and the substituted carbamate should be conducted in the presence of an acid catalyst. Representative examples of suitable acid catalysts include boron trifluoride, aluminum chloride, and methanesulfonic acid. Methanesulfonic acid is currently preferred. The acid catalyst is generally present in the reaction medium in the quantity of from about 0.05 moles to about 0.3 moles for every mole of substituted carbamate utilized.

The molar ratio of substituted carbamate to cyclopentadiene can vary widely, however it is generally in the range of from about 1 to about 4 moles of cyclopentadiene for every mole of substituted carbamate present.

The reaction is typically conducted in an organic solvent. Representative examples of suitable solvents include acetonitrile, toluene, ethylene dichloride and methylene chloride. It is also preferred that the reaction be conducted at a temperature range of from about 10° C. to about 80° C., and more preferrably from about 50°-70° C. for a period of time ranging from about 0.5 hours to about 6 hours.

The N-cyclopentenyl carbamate is preferrably recovered from the reaction zone prior to its utilization in the next step of the synthesis. It can be recovered by a variety of techniques which are analogously known in the art. One suitable technique is vacuum distillation. Another suitable technique is to isolate the N-cyclopentenyl carbamate by extraction from a biphasic solvent system. Suitable biphasic systems include methyl ethyl ketone/water, hexane/water, and toluene/ethylene glycol. The desired product can be found in the organic phase. The currently preferred method of purification in large scale synthesis is to dissolve the crude carbamate in hexane/methylene chloride and then extract this mixture with methanol/water/sodium chloride (60:40:2–40:60:2, more preferably 49:49:2).

The next step in the synthesis is to form a N-(2,3-epoxycyclopentyl) carbamate of the formula:

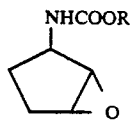

Formula V wherein R is as defined above in Formula IV. It is preferred for the 2,3-epoxy substituent to have a cis orientation.

An epoxy cylopentyl carbamate having the desired stereo-chemistry can be achieved by reacting the N-cyclopentenyl carbamate of Formula IV with a suitable epoxidizing agent such as, for example, an alkyl peracid, a peroxy aryl acid, and vanadium (v) oxide/t-butyl hydroperoxide. The alkyl peracid, peracetic acid, is currently utilized. The epoxidizing agent is generally present in the quantity of from about 1 to about 1.5 moles for every mole of N-cyclopentenyl carbamate utilized.

The reaction is typically conducted in an organic solvent such as, for example, methylene chloride, toluene, hexane, or dichloroethane.

The reaction is typically conducted at a temperature range of from about 10° C. to about 20° C. The reaction is generally allowed to proceed for a period of time ranging from about 1 hour to about 17 hours.

After the reaction is completed, the reaction mixture is typically treated with an organic or inorganic base such as sodium hydroxide, potassium hydroxide, lithium hydroxide, ammonium hydroxide, or triethyl amine. The N-(2,3-epoxy-cyclopentyl) carbamate will be located in the organic phase of this mixture. The crude epoxide can be utilized in the next step without further purification.

The cyclopentyl epoxide derivative is then reacted with a phenol in the presence of a strong base in order to form an oxazolone of the formula:

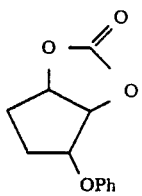

Formula VI wherein Ph represents a phenyl ring, which can optionally be substituted with up to 3 substituents selected from the group consisting of a ($C_1$–$C_6$) alkyl, a ($C_1$–$C_6$) alkoxy, halogen, nitro, trifluoromethyl, and trifluomethoxy.

The phenol utilized in the reaction with the epoxide should be structurally analogous to the phenyl substituent appearing in the desired oxazolone. It should also be structurally analogous to the phenyl substituent appearing in the desired 2-amino-5-phenoxycyclopentanol since it will be retained in the final product. Thus if the phenyl ring in the oxazolone is substituted with a chlorine at the para postition, then the phenol that is utilized should also be substituted with a chlorine at the para position, relative to the hydroxy group of the phenol. The phenol is typically present in the reaction medium in an equimolar quantity or preferably a molar excess relative to the N-(2,3-epoxy-cyclopentyl) carbamate.

It is necessary for a strong base to be present in the reaction also. Representative examples of strong bases include sodium hydroxide, potassium hydroxide, or lithium hydroxide. The quantity of strong base utilized will vary with whether the oxazolone will be separated from the reaction mixture or whether it will be hydrolyzed in-situ after its formation as described below. If the oxazolone will be recovered, then the strong base is generally present in the reaction medium in a quantity of from about 0.01 to about 0.2 moles for every mole of N-(2,3-epoxoycyclopentyl) carbamate present. If the oxazolone will be hydrolyzed in-situ after its formation, then generally from about 1 to about 3 moles of base will added for every mole of N-(2,3-epoxoy-cyclopentyl) carbamate present.

The reaction is typically conducted at a temperature range of from about 50° C. to about 80° C., for a period of time ranging from about 0.3 hours to about 18 hours. The reaction is also typically conducted in water.

If desired the oxazolone can be recovered and purified, prior to its further utilization in the reaction scheme. This can be accomplished by removing the solvent and subjecting the crude oxazolone to recrystalization. Acetonitrile is suitable for the recrystallization.

It is not necessary to conduct this additional recovery and purification. The oxazolone can be hydrolyzed in-situ after its formation. An additional quantity of strong base is generally added directly to the reaction mixture containing the oxazolone in order to insure the complete hydrolysis of the oxazolone into the desired 2-amino-5-phenoxycyclopentanol of Formula I.

Suitable strong bases for conducting this hydrolysis include sodium hydroxide, potassium hydroxide, and lithium hydroxide. The quantity of strong base added to the oxazolone to insure complete hydrolysis will generally be in the quantity of from about 1 mole to about 2 moles of base for every mole of oxazolone initially present and more preferably from about 1 mole to about 1.5 moles of base. The oxazolone and strong base are generally stirred together for a period of time ranging from about 2 to about 18 hours at a temperature range of from about 70° C. to about 80° C. to insure complete hydrolysis.

This hydrolysis produces a product where the 2-hydroxy substituent is cis and the 3-phenoxy substituent is trans, relative to the amine. This is the preferred stereochemical orientation of the 2-amino-5-phenoxycyclopentanol and thus constitutes a further advantage of the present invention.

The 2-amino-5-phenoxycyclopentanol can be recovered from the reaction zone by extraction with an organic solvent. Methylene chloride is currently utilized. The cyclopentanol can be purified via the following two step procedure. First, the organic solvent containing the cyclopentanol is acidified thereby causing the precipitation of crude aminocyclopentanol as its hydrochloride salt. The crude cyclopentanol is further purified via recrystallization from an ethanol/water solvent system. The free base can be obtained using standard techniques such as adding approximately one equivalent of an organic or inorganic base to the 2-amino-5-phenoxycyclopentanol hydrochloride.

The following examples are presented in order to further illustrate the invention, but should not be construed as limiting the invention in any manner.

EXAMPLE I

The purpose of this example is to demonstrate a method for preparing a N-cyclopentenyl alkyl carbamate.

To a solution of 75 g of methyl carbamate (1 mole), 19.6 g of methanesulfonic acid (0.1 mole), and 150 g of toluene at 75° C., is added 132 g of freshly distilled cyclopentadiene (2 moles) over a one hour period. Upon completion of the addition, the solution was heated for an additional one hour. The solution was then cooled to room temperature. After the solution had cooled, it was washed with 10% sodium hydroxide (100 g) and water (100 g) and the resulting organic layer was then concentrated at reduced pressure. The N-cyclopentenyl methyl carbamate was recovered by fractional distillation at a temperature of 100° C. and 0.5 mm Hg. 79.0 g of liquid N-Cyclopentenyl methyl carbamate was obtained (yield of 56%).

EXAMPLE II

The purpose of this example is to demonstrate a method for the production of N-(2,3-epoxycyclopentyl) alkyl carbamate.

To a solution of N-cyclopentenyl methyl carbamate (110 g, 0.68 moles), sodium acetate (10 g) and methylene chloride (629 g), maintained at a temperature range of from 10°-15° C. is added 155 g of 35% peracetic acid over a one hour period. The mixture was stirred at 14° C. for 24 hours. The reaction mixture was diluted with water (248 g) and then cautiously neutralized with 50% sodium hydroxide (187 g) and 30% sodium bisulfite (32 g). The organic layer and aqueous layers were separated and the organic layer was saved for further purification. The aqueous layer was extracted twice with 120 g of methylene chloride. The organic layers were then combined and concentrated at reduced pressures to afford the crude epoxide as a thick oil. 110 g of N-(2,3-epoxycyclopentenyl) methyl carbamate was obtained and utilized in the next step of the synthesis without further purification. An analytically pure sample was obtained by column chromatography using silica gel (stationary phase) and ethyl acetate/hexane (mobile phase). The N-(2,3-epoxycyclopentenyl) methyl carbamate was determined to have a melting point of 44°-45° C.

EXAMPLE III

The purpose of this example is to demonstrate a method for the preparation and purification of the oxazolone.

To a solution of 25 g of the crude N-(2,3-epoxycyclopentenyl) methyl carbamate (0.152 moles), 18.8 g of phenol (0.2 moles), and water (100 g) was added 1.6 g of sodium hydroxide (0.02 moles). The reaction mixture was then maintained at a temperature of 75° C. for 16 hours. The mixture was then allowed to cool to room temperature. The desired oxazolone separated from the reaction mixture as an oily layer. The oil was redissolved in methylene chloride and dried with sodium sulfate. The solvent was removed by concentration at reduced pressures affording a colorless oil. Recrystallization from acetonitrile afforded 13 g of phenoxyoxazolone (yield of 45%) having a melting point of 118°-119° C.

EXAMPLE IV

The purpose of this example is to demonstrate a method for the preparation of the oxazolone from the crude epoxide and the in-situ transformation of the oxazolone into the desired cis-hydroxy trans-phenoxycyclopentylamine.

110 g of crude N-(2,3-epxoycyclopentyl) methyl carbamate (0.68 moles) is added to a solution of 192 g of phenol (2.0 mole), 163 g of 50% sodium hydroxide (2 moles) and water (310 g). The reaction mixture was heated at approximately 74° C. for approximately 24 hours and an additional 81 g of sodium hydroxide was added. The reaction mixture was then heated for an additional period of time ranging from 12 to 18 hours and cooled to room temperature. The reaction mixture was then extracted 3 times with 300 g of methylene chloride. The resulting methylene chloride layers were combined and concentrated to a 25% solution (by weight). The solution was then charged with hydrogen chloride at a rate such that the temperature was maintained between 24°-30° C. until the solution was slightly acidic. The resulting precipitate was filtered, washed with methylene chloride and dried to afford 103.42 g of cis-hydroxy trans-phenoxycyclopentyl amine hydrochloride (66% yield).

I claim:

1. A compound of the formula:

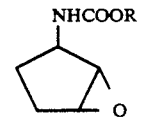

Formula V wherein R is represented by $C_1$-$C_{12}$ alkyl, phenyl, or phenyl substituted at up to 3 positions by $C_{1-6}$ alkoxy, nitro, trifluoromethyl, hydroxy or trifluoromethoxy.

2. A compound according to claim 1, wherein R is represented by a $C_1$-$C_6$ alkyl.

3. A compound according to claim 1, wherein R is represented by a $C_1$ alkyl.

4. A compound according to claim 1 wherein said 2,3-epoxy substituent is in a cis orientation.

* * * * *